(12) United States Patent
Harder

(10) Patent No.: US 10,390,944 B2
(45) Date of Patent: Aug. 27, 2019

(54) BRAIDED SUPPORT STRUCTURE

(71) Applicant: HLT, Inc., Maple Grove, MN (US)

(72) Inventor: Lucas Harder, Minneapolis, MN (US)

(73) Assignee: HLT, Inc., Maple Grove, MN (US)

( * ) Notice: Subject to any disclaimer, the term of this patent is extended or adjusted under 35 U.S.C. 154(b) by 78 days.

(21) Appl. No.: 15/098,090

(22) Filed: Apr. 13, 2016

(65) Prior Publication Data

US 2017/0296332 A1   Oct. 19, 2017

(51) Int. Cl.
*A61F 2/24* (2006.01)
*A61F 2/90* (2013.01)
*D04C 1/06* (2006.01)
*A61F 2/01* (2006.01)

(52) U.S. Cl.
CPC .......... *A61F 2/2412* (2013.01); *A61F 2/2418* (2013.01); *A61F 2/90* (2013.01); *D04C 1/06* (2013.01); *A61F 2/01* (2013.01); *A61F 2240/001* (2013.01); *D10B 2509/06* (2013.01)

(58) Field of Classification Search
CPC ......... A61F 2/24; A61F 2/01; A61F 2240/001
USPC ........................................................ 623/1.22
See application file for complete search history.

(56) References Cited

U.S. PATENT DOCUMENTS

| | | | |
|---|---|---|---|
| 5,383,925 A | 1/1995 | Schmitt | |
| 6,136,023 A | 10/2000 | Boyle | |
| 8,151,682 B2 | 4/2012 | Lilburn et al. | |
| 2012/0065728 A1* | 3/2012 | Gainor | A61F 2/2436 623/2.11 |
| 2016/0000443 A1* | 1/2016 | Lilburn | A61B 17/122 606/158 |

OTHER PUBLICATIONS

WIPO, U.S. International Search Authority, International Search Report and Written Opinion dated May 30, 2017 in International Patent Application No. PCT/US2017/024301, 16 pages.

\* cited by examiner

*Primary Examiner* — Christopher D. Prone
*Assistant Examiner* — Tiffany P Shipmon
(74) *Attorney, Agent, or Firm* — Inskeep IP Group, Inc.

(57) ABSTRACT

A braided support structure that folds upon release from a delivery device wherein said fold is at least partially effected by varying the pic angle of the braids at locations where the folding is desired.

6 Claims, 3 Drawing Sheets

Radialy Stiff
Axialy Compliant

Radialy Compliant
Axialy Stiff

Radialy Neutral
Axialy Neutral

BRAIDED SUPPORT STRUCTURE

BACKGROUND OF THE INVENTION

Cardiovascular implants are preferably delivered percutaneously in order to reduce patient trauma, reduce the trauma endured by the patient and significantly reduce recovery periods. Through the use of one or more catheters that are introduced through, for example, the femoral artery, tools and devices can be delivered to a desired area in the cardiovascular system to perform many number of complicated procedures that normally otherwise require an invasive surgical procedure. The percutaneous approach is particularly attractive as an alternative to performing open-heart surgery.

Valve replacement surgery provides one example of an area where percutaneous solutions are being developed. A number of diseases result in a thickening, and subsequent immobility or reduced mobility, of heart valve leaflets. Such immobility also may lead to a narrowing, or stenosis, of the passageway through the valve. The increased resistance to blood flow that a stenosed valve presents can eventually lead to heart failure and ultimately death.

In the case of an aortic valve replacement, a catheter is inserted into the femoral artery and navigated, with or without a guidewire, through the artery, around the aortic arch, and into the heart at the location of the aortic valve. The ease with which the catheter is navigated greatly increases with a reduction in catheter size. In order to reduce catheter size, however, implants having a small delivery profile are required. These implants must be able to expand to the size of the native anatomical feature, such as the aortic valve, in order to be effective.

One solution that has been developed is a prosthetic valve attached to a braided support structure. This device is shown and described in several Patents and Published Applications including U.S. Pat. No. 8,974,523, issued Mar. 10, 2015 to Thill et al., incorporated by reference herein. The braided support structure is a tubular mesh that is capable of being delivered via a very small diameter delivery catheter. The tubular mesh is formed one or more fine strands braided or woven together into an elongate tube. The strands may be fibrous, non-fibrous, multifilament, or monofilament. The strands exhibit shape memory such that the elongate tube may be formed into a desired folded shape, then stretched out into a very small diameter, elongated configuration. The small diameter, elongated configuration makes a very small diameter delivery catheter possible.

Upon deployment, the elongated tube is slowly pushed out of the delivery catheter, where it gradually regains its folded, constructed configuration. The tube conforms to the internal geometries of the target vessel. In addition, the braid effectively traps all emboli that may be released from the vessel walls.

As the tube continues to be pushed from the delivery catheter, it begins to fold in upon itself as it regains its constructed configuration. As it folds in upon itself, the forces exerted by each layer add together, making the structure incrementally stronger. Thus, varying levels of strength may be achieved without changing the elongated diameter of the device.

Using this folded tube, the valve can be attached such that the valve or other structure (such as a filter) in its elongated configuration within the delivery catheter does not reside within the elongated tube, but on deployment can be positioned in, above or below the tube.

In order to get this device to fold upon exiting the catheter, preformed folds are heat-set into the braided tube during manufacturing. These folds are then unfolded during the loading process. While in the catheter, the preformed folds are unable to re-fold due to the constraints placed on the device by the catheter.

The degree to which the device tends to assume a folded configuration upon exiting the catheter is a factor in the ease of device delivery. If the device does not fold completely upon delivery, an additional step of pulling the distal end of the device while pushing the proximal end of the device can be performed in order to effect the folding. However, it would be desirable if this added step were unnecessary.

Furthermore, heat setting the device is done to create an annealed configuration of the folds. However, it has been determined that the pic angles of the wires determine how strong the tendency is to fold. With this in mind, it would be desirable to develop a way to improve the ease with which the device may be unfolded while retaining a strong tendency to fold upon delivery.

SUMMARY OF THE INVENTION

The inventions described herein pertain to providing a braided tubular support structure that has zones or areas of varying radial and axial compliance. These areas are created by changing an angle at which the wires intersect each other, also referred to herein as a pic angle. By way of convention, the pic angle referred to herein will be measured against a longitudinal axis of the tubular device.

More specifically, it has been found that increasing the pic angle, such that the wires of the braid are directed in a more circumferential direction rather than a longitudinal direction, increases radial stiffness and axial compliance, resulting in greater ease of folding. Conversely, decreasing the pic angle, such that the wires of the braid are directed in a more longitudinal direction, increases radial compliance and axial stiffness.

Radial compliance results in greater folding difficulty but allows for ease in compression into a catheter. Thus, by locally modifying the braid angle of a wire braid or weave, the stiffness of the tubular structure can be changed within a given length of the tube. In a cylindrical weave pattern, the inverse relationship between radial stiffness and axial stiffness can thus be exploited in specific regions to promote motion or interaction of the implant with its surroundings. Additionally, by combining areas of both increased and decreased pic angle, a tubular braided device may be created that combines ease of unfolding, folding strength, as well as compressibility for loading into a delivery catheter.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1A:
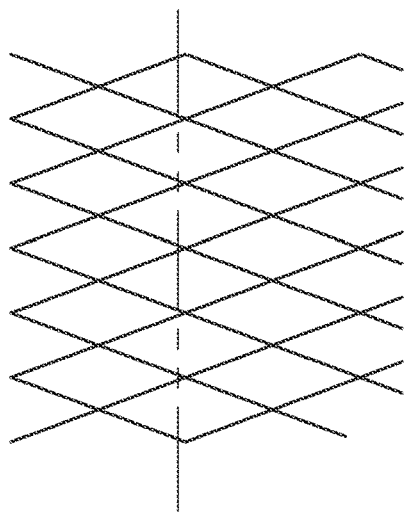
FIG. 1A is a braid that has a pic angle that is larger than 45.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 1B:
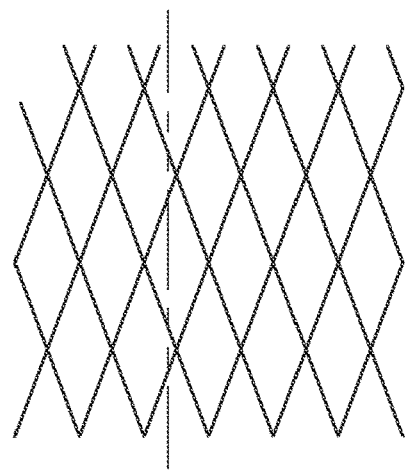
FIG. 1B is a braid that has a pic angle that is less than 45 degrees.
Figure 1C:
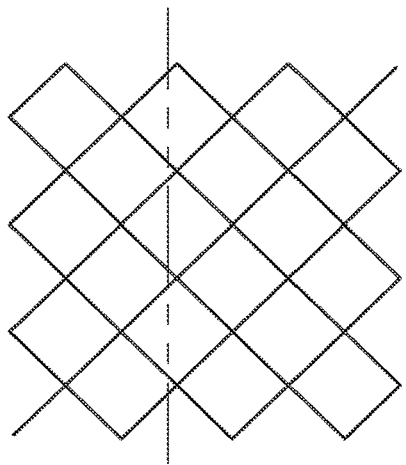
FIG. 1C is a braid that has a pic angle that is 45 degrees.

FIG. 1A, FIG. 1B and FIG. 1C comprise a chart showing braids with three general categories of pic angles and is shown for purposes of convention. Pic angle is being measured against a longitudinal axis of the braided device, which is shown as a horizontal axis line in FIG. 1A, FIG. 1B and FIG. 1C. The pic angle in FIG. 1A ("pic angle A") is larger than 45 degrees. A braid having pic angle A exhibits radial stiffness and axial compliance.

The braid shown in FIG. 1B has a pic angle that is less than 45 degrees. A braid having pic angle B exhibits radial compliance and is axially stiff. Axial stiffness results in a resistance to folding due to the increased spacing density of the wires circumferentially. Additionally, as the pic angle decreases, folds involve bending the wires rather than rolling the wires over each other in the braid. This can be easily envisioned if one pictures a tube of longitudinally-aligned wires, thus having a pic angle of 0. To fold this tube, each wire would have to bend 180 degrees. Conversely, a tube formed of wires that are nearly circumferentially oriented, or having a pic angle close to 90 degrees, would fold easily as the wires would have to bend very little.

The braid of FIG. 1C has a pic angle that is 45 degrees. It is provided as an example of braid that is axially and radially neutral.

Figure 2:
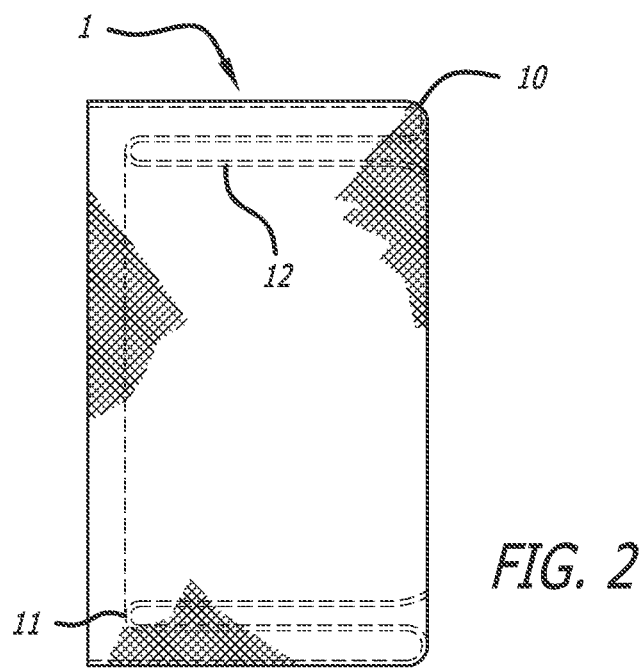
FIG. 2 is an embodiment of the invention in a folded configuration.

FIG. 2 shows an embodiment of a device 1 of the invention in a folded state. The device 1 has two folds, fold 10 and fold 11. The folds are separated by unfolded areas, such as area 12.

During loading into a delivery catheter, the device 1 is collapsed into an unfolded, elongated cylinder. Elongating the device 1 stretches the braids such that the wires move relative to each other and the pic angles all tend toward a shallower state. This change in pic angle is referred to herein as "compressive deformation." Compressive deformation during loading will cause a pic angle A to tend toward a neutral pic angle C, and a pic angle C toward a pic angle B.

For example, if in a relaxed state the tubular structure 1 has a pic angle C of 45 degrees, then as the tubular structure is compressed, the pic angle will decrease to less than 45 degrees and will thus fall into the category of pic angle B. Conversely, if the tubular structure is expanded, the pic angle will increase to greater than 45 degrees and will thus fall into the category of pic angle A.

Figure 3:
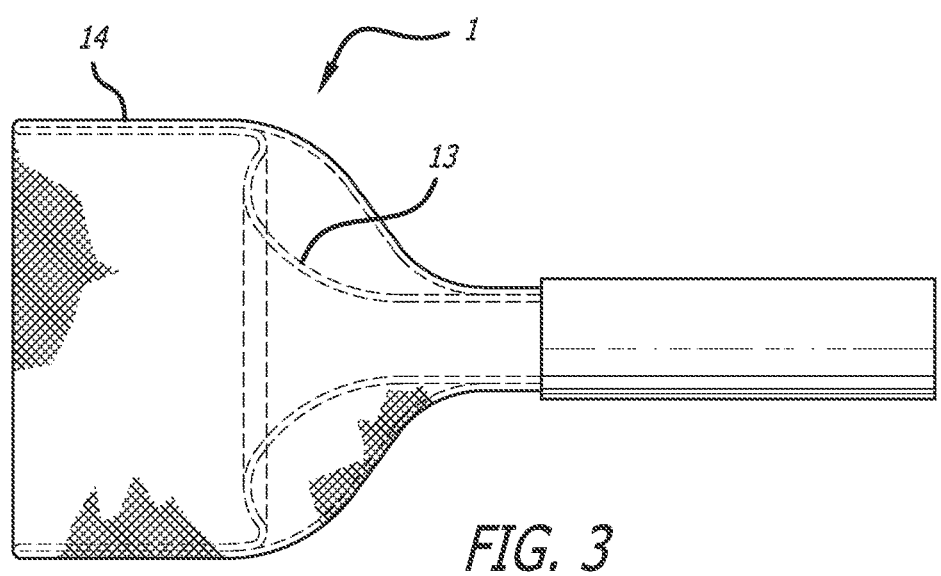
FIG. 3 is an embodiment of the invention exiting a delivery device.

If this compression did not occur, the structure's wires within the braid would undergo a significant amount of bending to accommodate the folding process, which would take more force. Thus, to promote the folding process the area adjacent to the folds 10 and 11, such as area 13 in FIG. 3, would preferably have a pic angle A.

In locations that encounter axial loads once deployed, such as those placed on the device by blood flow, or in areas where minimal deformation is desired, a shallow pic angle B is used to promote axial stiffness. For example, referring to FIG. 2, location 12 would benefit from a pic angle B such that interactions and pressures from blood flow do not cause compressive motion within the layer. Similarly, location 14 in FIG. 3 would benefit from pic angle B in order to promote a ridged axial reference during the folding process of the implant.

For purposes of folding, such as at locations 10 and 11 of FIG. 2, it has been found that a pic angle of about 60 degrees or greater will effect the fold. Recall that, as stated above, increasing the radius of the tubular structure will increase the pic angle. It follows that as the tubular structure expands, areas of the tubular structure that achieve a pic angle of about 60 degrees first, will begin to invert or fold in on themselves.

Variances in pic angle are not simply a result of selective expansion and compression of the tubular structure. The variances are specifically woven into the braid. The process of acute braid angle change can be applied during the braiding process by providing features, such as pins, on the braiding mandrels used to create the braid that the wire being braided can be bent around to change the pic angle. Alternatively, the variances in pic angle can be achieved by manually moving the individual wires within the braid after the braid has been heat set.

For example, heat setting the braid causes deformation of the wires against each other, which forms peaks and valleys to form in the wires. In other words, if the wires are woven together and then unwoven, the wires will remain relatively straight. However, during the process of heat setting, each wire is deformed against the intersecting wires to form peaks and valleys that correspond to the intersections.

Figure 4:
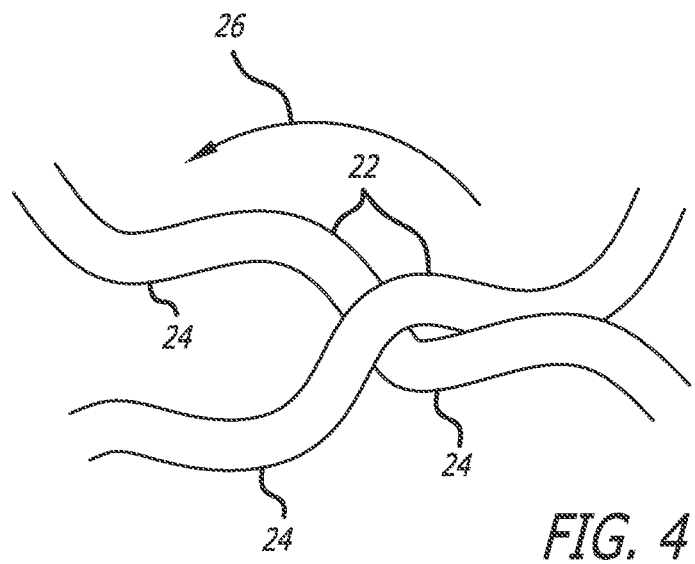
FIG. 4 is a close-up view of an embodiment of an intersection of two filaments of a braid of the invention.

Referring to FIG. 4, it has been found that these peaks 22 and valleys 24 can be used to change pic angle. By manually moving a peak 22a from a corresponding valley 24a to an adjacent valley 24b, as shown by the arrow 26, the interference between the peaks and valleys will prevent the displaced peak 22a from returning to the original valley 24a. This results in a change of pic angle.

Figure 5:
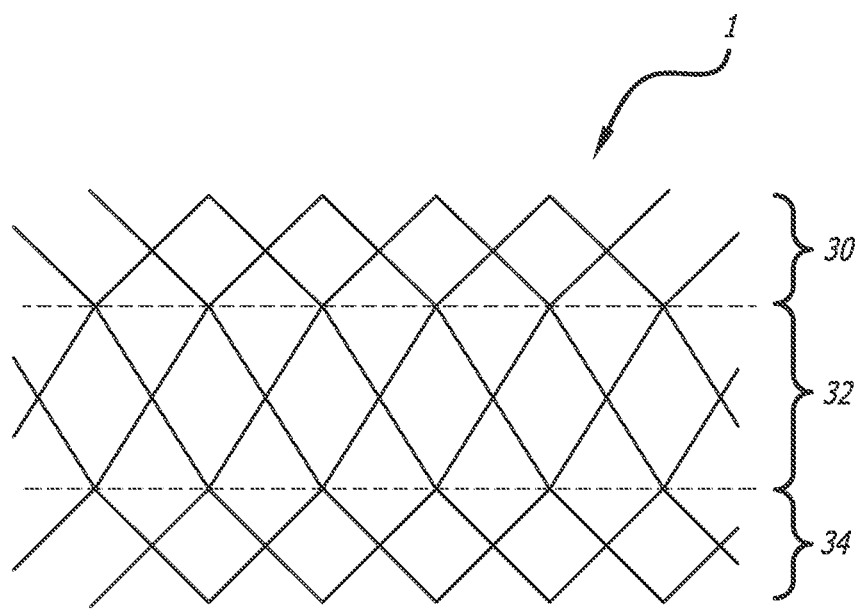
FIG. 5 is a plan view of a braided device having regions of varying pic angles.

FIG. 5 shows a device 1 having regions 30, 32 and 34 having different pic angles. These regions may be formed by either providing features in the braiding mandrels during the original weaving process, or by using the peak and valley displacement method discussed above.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A braided tubular medical implant comprising:
   a braided tubular structure having a first configuration and a second configuration wherein the first configuration is an elongated, unfolded configuration and the second configuration is a deployed, folded configuration;
   wherein said braided tubular structure includes:
   at least one circumferential preformed fold area having wires intersecting at a first braid angle;
   a preformed circumferential fold located within said circumferential preformed fold area;

at least one body area adjacent said circumferential preformed fold area in which said wires intersect at a second braid angle;

wherein said first braid angle is not equal to said second braid angle; and, wherein the first braid angle being not equal to the second braid angle at least partially effects folding the braided tubular structure to form said second configuration.

2. The braided tubular medical implant of claim 1 wherein said second braid angle is greater than said first braid angle.

3. The braided tubular medical implant of claim 1 wherein said second braid angle is greater than 45 degrees and said first braid angle is less than 45 degrees.

4. A braided tubular support structure comprising:

a first end;

a second end;

a first portion having wires intersecting at a first braid angle;

a preformed circumferential fold line located within said first portion;

a second portion in which said wires intersect at a second braid angle that is different from said first braid angle;

wherein locations of said first portion and said second portion, and the difference between the second braid angle and the first braid angle, are selected to effect a folding of said braided tubular support structure along said fold line when released from a delivery catheter.

5. The braided tubular medical implant of claim 4 wherein said second braid angle is greater than said first braid angle.

6. The braided tubular medical implant of claim 4 wherein said second braid angle is greater than 45 degrees and said first braid angle is less than 45 degrees.

\* \* \* \* \*